United States Patent
Hotta et al.

(10) Patent No.: US 11,918,396 B2
(45) Date of Patent: Mar. 5, 2024

(54) MEDICAL IMAGING APPARATUS

(71) Applicant: Canon Medical Systems Corporation, Otawara (JP)

(72) Inventors: Aira Hotta, Kawasaki (JP); Takashi Sasaki, Yokohama (JP); Yuko Kizu, Yokohama (JP); Shinichi Uehara, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 790 days.

(21) Appl. No.: 16/045,209

(22) Filed: Jul. 25, 2018

(65) Prior Publication Data
US 2019/0038246 A1    Feb. 7, 2019

(30) Foreign Application Priority Data

Aug. 1, 2017  (JP) .................................. 2017-148873

(51) Int. Cl.
*A61B 5/00*    (2006.01)
*A61B 5/055*   (2006.01)
(Continued)

(52) U.S. Cl.
CPC .......... *A61B 6/4447* (2013.01); *A61B 5/0033* (2013.01); *A61B 5/055* (2013.01);
(Continued)

(58) Field of Classification Search
CPC ..... A61B 5/0033; A61B 5/055; A61B 5/7445; A61B 6/032; A61B 6/04; A61B 6/4447;
(Continued)

(56) References Cited

U.S. PATENT DOCUMENTS 5,864,331 A  *  1/1999  Anand ..................... G09G 5/00
                                                345/656
8,837,051 B1 *  9/2014  Olczak ............... G02B 27/0172
                                                359/630
(Continued)

FOREIGN PATENT DOCUMENTS

JP       58-17429 A     2/1983
JP     2008-64911 A     3/2008
(Continued)

OTHER PUBLICATIONS

Japanese Office Action dated Aug. 10. 2021 in Japanese Patent Application No. 2017-148873, 3 pages.
(Continued)

*Primary Examiner* — Christopher L Cook
(74) *Attorney, Agent, or Firm* — Oblon, McClelland, Maier & Neustadt, L.L.P.

(57) ABSTRACT

According to one embodiment, a medical imaging apparatus includes a gantry, a carriage, a screen, a reflector, and a frame. The gantry has a bore formed therein. The bore is formed to accept a subject to be imaged by the medical imaging apparatus. The carriage moves through the bore. The screen is provided on the carriage. An image is projected on the screen by a projector from a rear. The rear is opposite to a side of which a top plate is inserted into the bore. The reflector reflects the image projected on the screen. The reflector includes prisms arranged in a same line. The frame supports the reflector. The frame is provided on the carriage.

9 Claims, 10 Drawing Sheets

(51) Int. Cl.
  *A61B 6/00*      (2006.01)
  *G01R 33/28*     (2006.01)
  *G02B 3/08*      (2006.01)
  *G03B 21/14*     (2006.01)
  *G03B 21/28*     (2006.01)
  *G03B 21/56*     (2006.01)
  *G03B 29/00*     (2021.01)
  *A61B 6/03*      (2006.01)
  *A61B 6/04*      (2006.01)
  *G02B 5/10*      (2006.01)

(52) U.S. Cl.
  CPC ............ *A61B 5/7445* (2013.01); *A61B 6/462* (2013.01); *G01R 33/283* (2013.01); *G02B 3/08* (2013.01); *G03B 21/142* (2013.01); *G03B 21/28* (2013.01); *G03B 21/56* (2013.01); *G03B 29/00* (2013.01); *A61B 6/032* (2013.01); *A61B 6/04* (2013.01); *G02B 5/10* (2013.01)

(58) Field of Classification Search
  CPC ........ A61B 6/462; G01R 33/283; G02B 1/11; G02B 3/08; G02B 5/0833; G02B 5/10; G02B 5/12; G03B 21/142; G03B 21/28; G03B 21/56; G03B 29/00
  See application file for complete search history.

(56) References Cited

U.S. PATENT DOCUMENTS

| | | | |
|---|---|---|---|
| 2002/0167725 A1* | 11/2002 | Goto | G03B 21/625 |
| | | | 359/456 |
| 2010/0182236 A1* | 7/2010 | Pryor | H04N 9/3129 |
| | | | 345/158 |
| 2016/0313634 A1 | 10/2016 | Hotta et al. | |
| 2016/0313635 A1 | 10/2016 | Sasaki et al. | |
| 2017/0119320 A1 | 5/2017 | Ueda et al. | |
| 2017/0129272 A1* | 5/2017 | Rich | B42D 25/425 |
| 2017/0242260 A1* | 8/2017 | Song | G02B 30/27 |
| 2018/0101087 A1* | 4/2018 | Shinohara | G02B 6/0051 |

FOREIGN PATENT DOCUMENTS

| | | |
|---|---|---|
| JP | 2016-202514 | 12/2016 |
| JP | 2016-202515 | 12/2016 |
| JP | 2017-26866 A | 2/2017 |
| JP | 2017-80298 | 5/2017 |
| JP | 2017-093949 A | 6/2017 |

OTHER PUBLICATIONS

Japanese Office Action dated Nov. 2, 2021, issued in Japanese Patent Application No. 2017-148873.

* cited by examiner

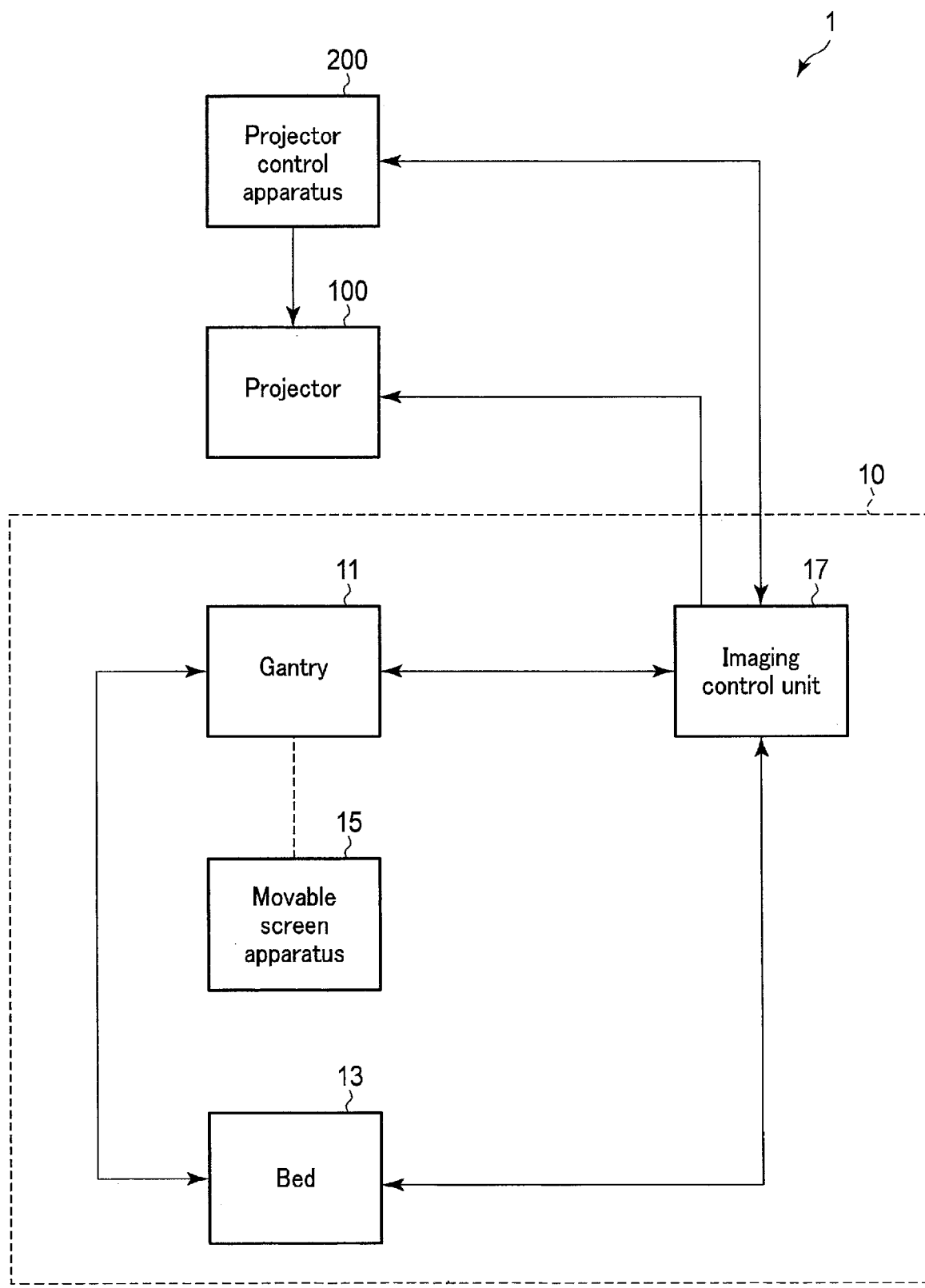
F I G. 1

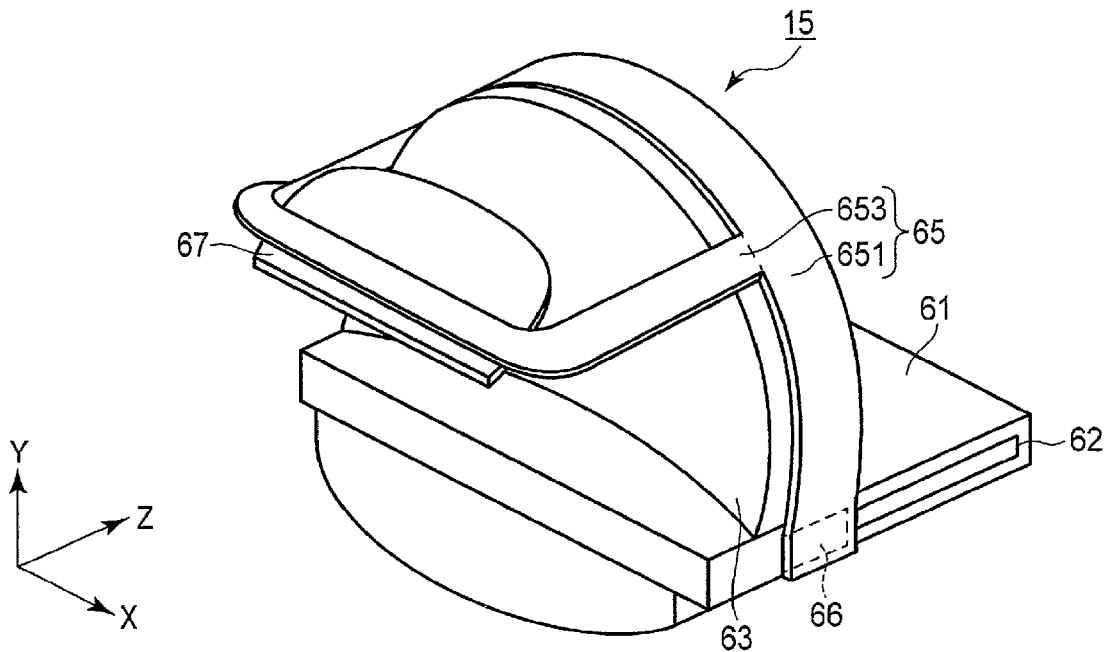
F I G. 3
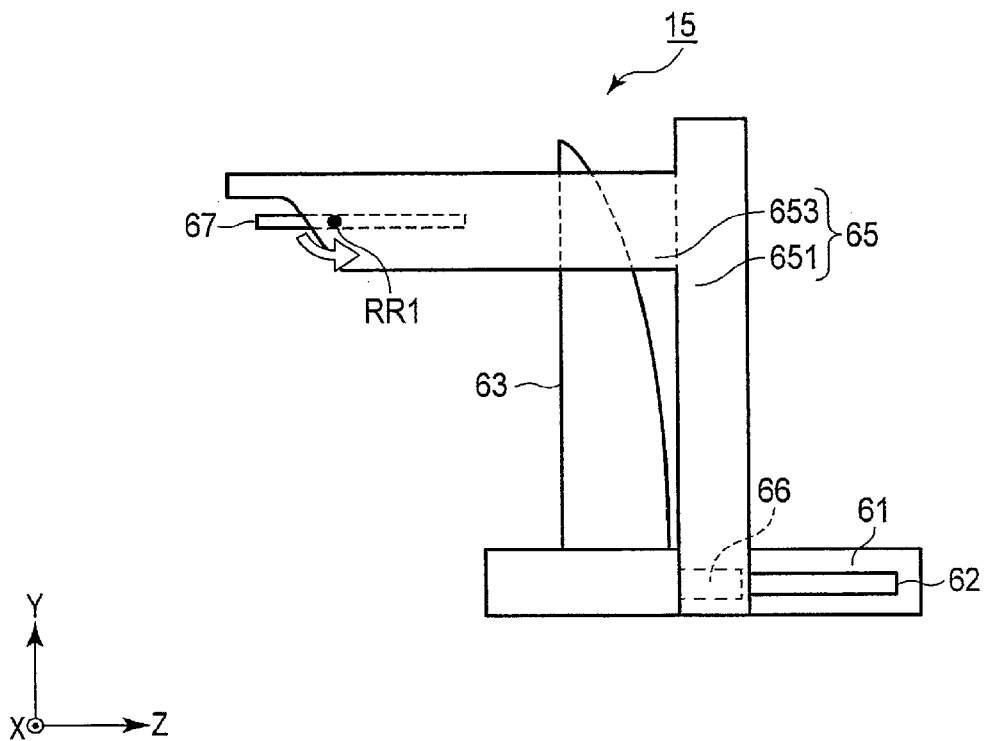
F I G. 4

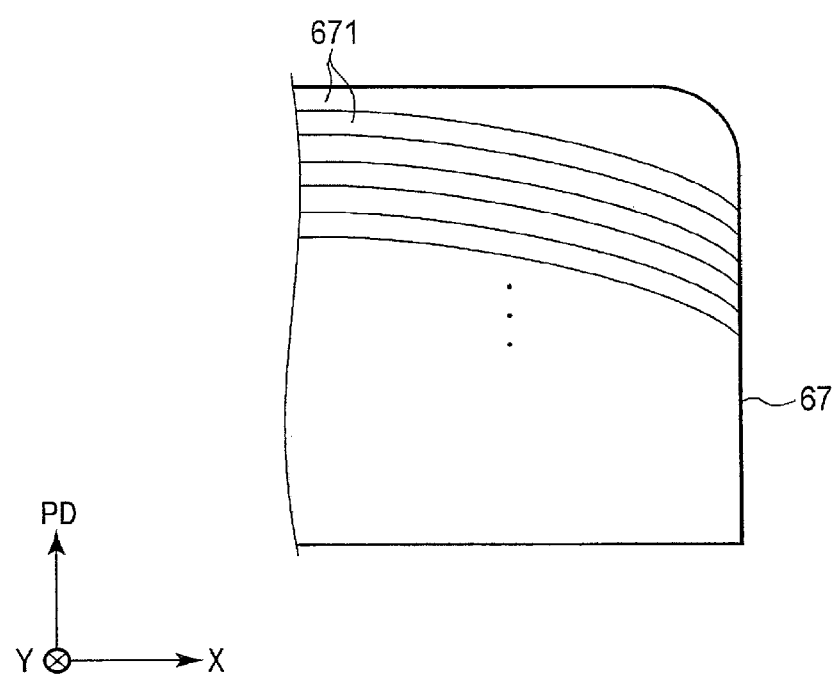
F I G. 9

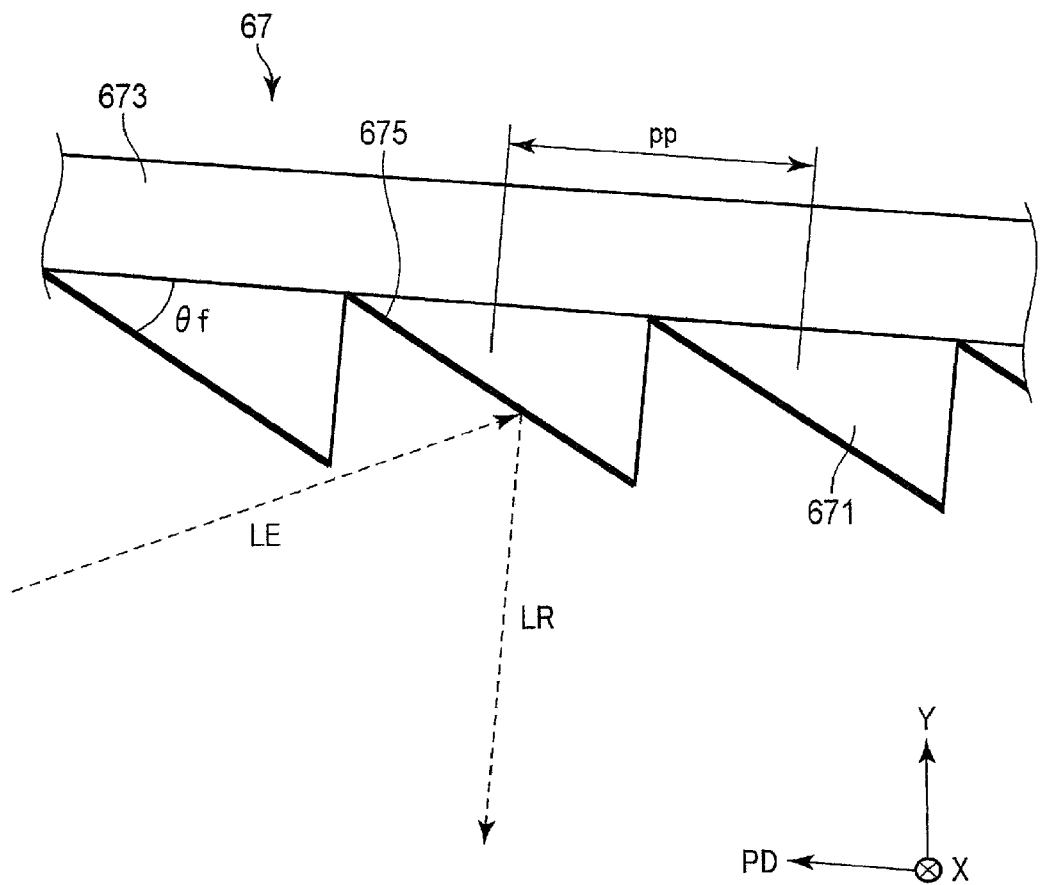
F I G. 10

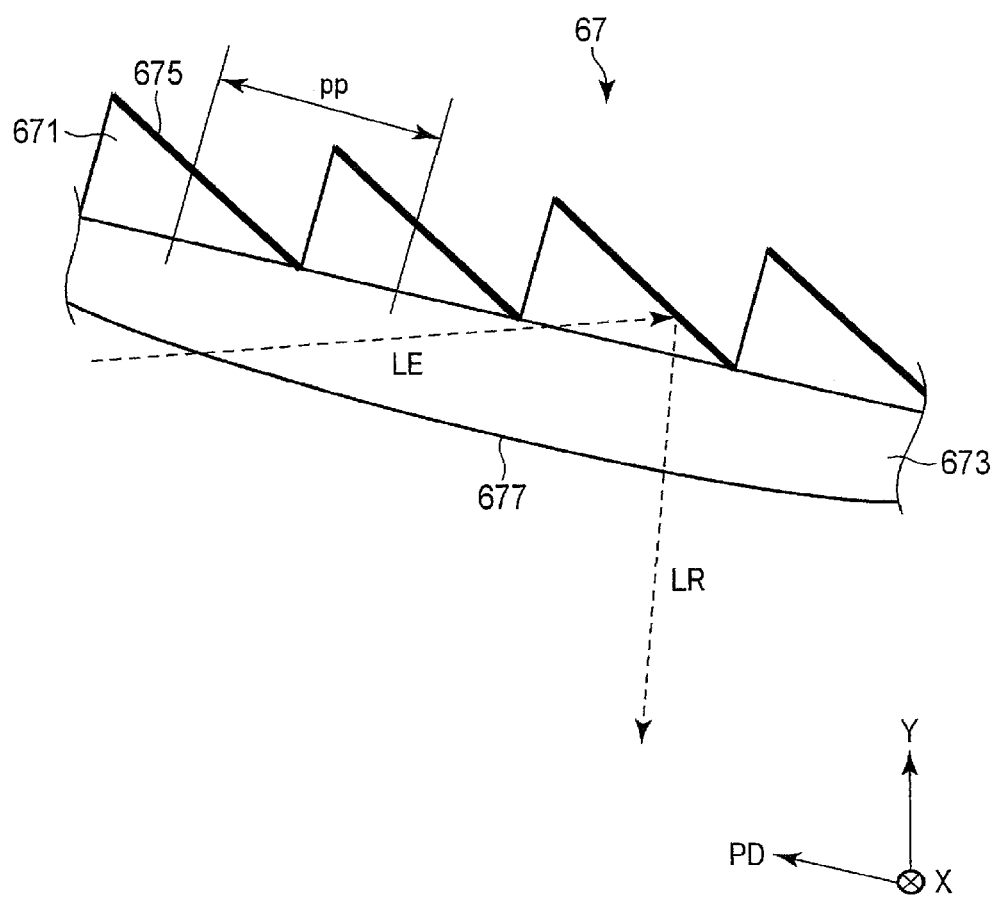
F I G. 11

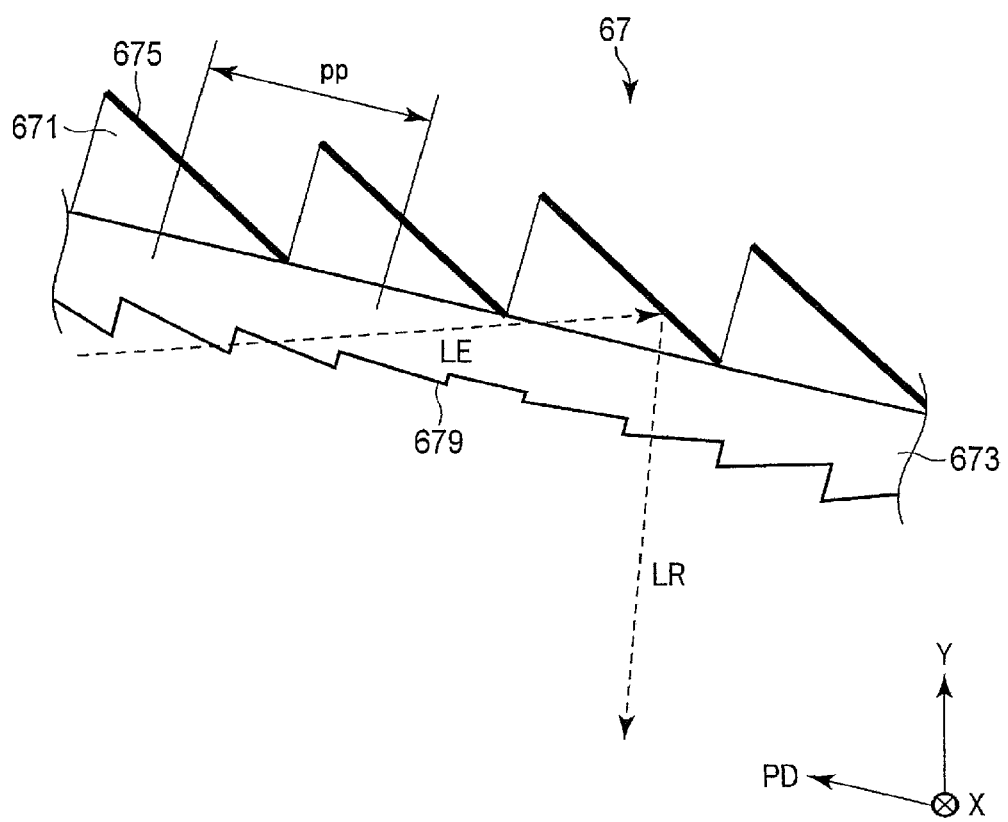
F I G. 12

MEDICAL IMAGING APPARATUS

CROSS-REFERENCE TO RELATED APPLICATIONS

This application is based upon and claims the benefit of priority from the prior Japanese Patent Application No. 2017-148873, filed Aug. 1, 2017, the entire contents of which are incorporated herein by reference.

FIELD

Embodiments described herein relate generally to a medical imaging apparatus.

BACKGROUND

A magnetic resonance imaging (hereinafter referred to as an MRI) apparatus is an apparatus for non-invasively acquiring a tomographic image of a patient using nuclear magnetic resonance. An MRI apparatus does not cause radiation exposure, and is capable of acquiring three-dimensional data of an affected area in high-resolution and therefore is widely used at medical sites.

The MRI apparatus includes a gantry equipped with an imaging mechanism such as a magnet. A bore having a substantially hollow shape is formed in the gantry. An MR imaging is performed in a state where a patient is inserted inside the bore. A gantry having a relatively large bore diameter has been developed; however, some patients feel stressed by an MR examination due to the long time it takes for MR imaging, noise while the gantry is driven, and a sense of pressure and being blocked inside the bore. Patients with a fear of confined spaces in particular may not be able to endure the environment inside an imaging space in the MRI apparatus. Therefore, in many cases, patients with a fear of confined spaces cannot be examined by the MRI apparatus.

BRIEF DESCRIPTION OF THE DRAWINGS

FIG. 1 shows a configuration of a medical image diagnostic system that includes a medical imaging apparatus according to a present embodiment.

FIG. 3 is a perspective view of a movable screen apparatus according to the present embodiment.

FIG. 4 is a side view of the movable screen apparatus according to the present embodiment.

FIG. 9 is a view of viewing the reflector including a plurality of prisms curved in a one-dimensional direction from the placement surface side of the top plate according to the present embodiment.

FIG. 10 is an arrow cross-sectional view taken along line FP-FP of FIG. 5 and FIG. 8 in the present embodiment.

FIG. 11 is an arrow cross-sectional view taken along line FP-FP of FIG. 5 and FIG. 8 in an applied example of the present embodiment.

FIG. 12 is an arrow cross-sectional view taken along line FP-FP of FIG. 5 and FIG. 8 in the applied example of the present embodiment.

DETAILED DESCRIPTION

Figure 2:
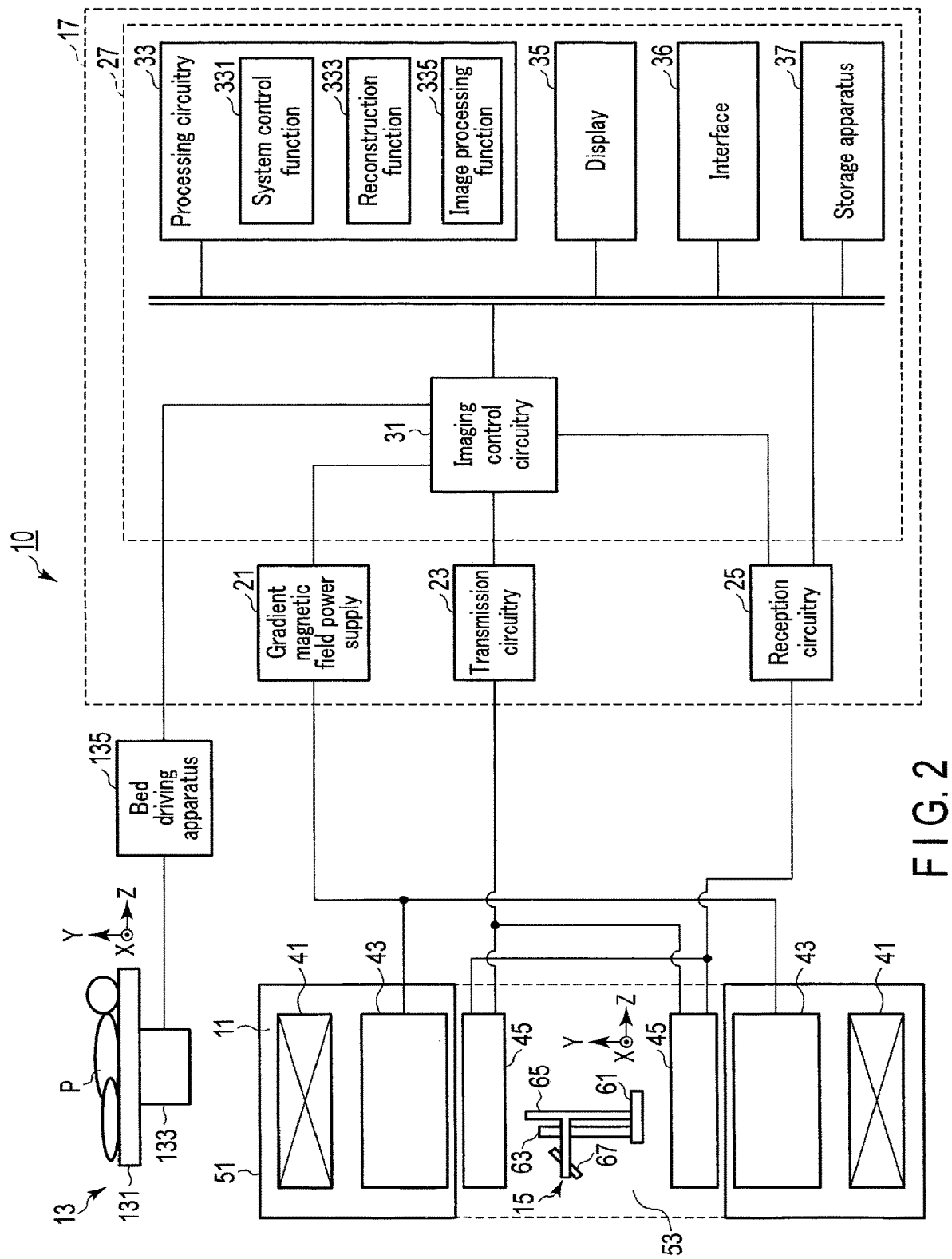
FIG. 2 shows a configuration of a magnetic resonance imaging apparatus according to the present embodiment.

In general, according to one embodiment, a medical imaging apparatus includes a gantry, a carriage, a screen, a reflector, and a frame. The gantry has a bore formed therein. The bore is formed to accept a subject to be imaged by the medical imaging apparatus. The carriage moves through the bore. The screen is provided on the carriage. An image is projected on the screen by a projector from a rear. The rear is opposite to a side of which a top plate is inserted into the bore. The reflector reflects the image projected on the screen. The reflector includes prisms arranged in a same line. The frame supports the reflector. The frame is provided on the carriage.

The object is to reduce a subject's sense of being blocked inside the bore of the gantry.

Hereinafter, the medical imaging apparatus according to the present embodiment will be explained with reference to the accompanying drawings. In the explanations below, structural elements having substantially the same functions and configurations will be denoted by the same reference symbols, and repetitive explanations of such elements will be given only when necessary.

FIG. 1 shows a configuration of a medical image diagnostic system 1 including a medical imaging apparatus 10 according to the present embodiment. As shown in FIG. 1, the medical image diagnostic system 1 includes the medical imaging apparatus 10, a projector 100, and a projector control apparatus 200 which are connected communicatably in a wired or wireless manner with each other. The medical imaging apparatus 10 includes a gantry 11, a bed 13, a movable screen apparatus 15, and an imaging control unit 17. The gantry 11 is equipped with a medical imaging mechanism configured to realize medical imaging. For example, a bore having a hollow shape is formed in the gantry 11. The bore is formed to accept a subject to be imaged by the medical imaging apparatus 10. The bore may have, for example, an opened shape of approximately 70 cm. The gantry 11 may have an opened imaging space instead of the bore. The bed 13 is installed at the front side of the gantry 11. The bed 13 supports, in a freely movable manner, a top plate on which a subject P is placed. The bed 13 moves the top plate according to control through the gantry 11, a console, and the like. The movable screen apparatus 15 is movably provided in the bore of the gantry 11. The projector 100 is installed at the rear side of the gantry 11. An image from the projector 100 is projected on the movable screen apparatus 15.

The projector control apparatus 200 is a computer apparatus that controls the projector 100. The projector control apparatus 200 supplies data relating to an image to be projected to the projector 100.

The projector 100 projects the image corresponding to the data supplied from the projector control apparatus 200 on a screen of the movable screen apparatus 15.

The imaging control unit 17 functions as a hub of the medical imaging apparatus 10. For example, the imaging control unit 17 controls the gantry 11 in order to perform the medical imaging. In addition, the imaging control unit 17 reconstructs a medical image relating to the subject P based on data collected by the gantry 11 in the medical imaging. The imaging control unit 17 may also be configured to be capable of controlling the projector 100 via the projector control apparatus 200. Also, the configuration of the medical image diagnostic system 1 according to the present embodiment is not limited to the above-described configuration.

The medical image diagnostic system 1 according to the present embodiment can enhance the ability to remain inside the bore during the medical imaging according to the medical imaging apparatus 10 by utilizing the projector 100 and the movable screen apparatus 15. Any apparatus that can image the subject P using the gantry 11 in which a bore is formed may be used as the medical imaging apparatus 10 according to the present embodiment. Specifically, a single modality such as a magnetic resonance imaging (MRI) apparatus, an X-ray computed tomography (CT) apparatus, a positron emission tomography (PET) apparatus, and a single photon emission computed tomography (SPECT) apparatus can be applied as the medical imaging apparatus 10 according to the present embodiment. Alternatively, a combined modality such as an MR/PET apparatus, a CT/PET apparatus, an MR/SPECT apparatus, and a CT/SPECT apparatus may be applied as the medical imaging apparatus 10 according to the present embodiment. In order to provide the following explanation in detail, the medical imaging apparatus 10 according to the present embodiment is assumed to be an MRI apparatus 10. In addition, the medical image diagnostic system 1, which includes the MRI apparatus 10, the projector 100, and the projector control apparatus 200, will be referred to as an MRI system 1.

FIG. 2 shows the configuration of the MRI apparatus 10 according to the present embodiment. As shown in FIG. 2, the MRI apparatus 10 includes the imaging control unit 17, the gantry 11, the bed 13, and the movable screen apparatus 15. The imaging control unit 17 includes a gradient magnetic field power supply 21, transmission circuitry 23, reception circuitry 25, and a console 27. The console 27 includes imaging control circuitry 31, processing circuitry 33, a display 35, an interface 36, and a storage apparatus 37. The imaging control circuitry 31, the processing circuitry 33, the display 35, the interface 36, and the storage apparatus 37 are connected to be capable of communicating with each other via a bus. The gradient magnetic field power supply 21, the transmission circuitry 23, and the reception circuitry 25 are provided separately from the console 27 and the gantry 11.

The gantry 11 includes a static magnet field magnet 41, a gradient coil 43, and an RF coil 45. In addition, the static magnet field magnet 41 and the gradient coil 43 are housed in a housing (hereinafter referred to as a gantry housing) 51 of the gantry 11. The MRI apparatus 10 may have a hollow, cylindrical-shaped shim coil provided between the static magnet field magnet 41 and the gradient coil 43. A bore 53 having a hollow shape is formed in the gantry housing 51. The RF coil 45 is arranged inside the bore 53 of the gantry housing 51. In addition, the movable screen apparatus 15 according to the present embodiment is arranged inside the bore 53 of the gantry housing 51.

The static magnet field magnet 41, the gradient coil 43, and the RF coil 45, etc. correspond to the medical imaging mechanism. In the case where the medical imaging apparatus 10 is a modality of various types, such as the CT apparatus, the PET apparatus, the SPECT apparatus, the CT/PET apparatus, the MR/PET apparatus, the MR/SPECT apparatus, and the CT/SPECT apparatus, the medical imaging mechanism corresponds to a set of various types of imagining devices that is equipped on a gantry in such modality.

The static magnet field magnet 41 has a hollow and substantially cylindrical shape, and generates a static magnetic field therein. As the static magnet field magnet 41, for example, a permanent magnet, a superconducting magnet, or a normal conducting magnet is used. The central axis of the static magnet field magnet 41 is defined as a Z-axis; an axis vertically perpendicular to the Z-axis is referred to as a Y-axis; and an axis horizontally perpendicular to the Z-axis is referred to as an X-axis.

The gradient coil 43 is a coil unit mounted on the inner side of the static magnet field magnet 41 and formed into a hollow and substantially cylindrical shape. The gradient coil 43 generates a gradient magnetic field upon receiving a current supplied from the gradient magnetic field power supply 21.

The gradient magnetic field power supply 21 supplies a current to the gradient coil 43, in accordance with control by the imaging control circuitry 31. By supplying the current to the gradient coil 43, the gradient magnetic field power supply 21 causes the gradient coil 43 to generate a gradient magnetic field.

The RF coil 45 is arranged on the inner side of the gradient coil 43. The RF coil 45 receives an RF pulse supplied from the transmission circuitry 23 and generates a high frequency magnetic field. The high frequency magnetic field generated from the RF coil 45 oscillates with a resonant frequency unique to a target atomic nucleus and excites the target atomic nucleus that exists inside the subject P. The RF coil 45 receives a magnetic resonance signal (hereinafter referred to as an MR signal), which is emitted from the excited target atomic nucleus. The received MR signal is supplied to the reception circuitry 25 in a wired or wireless manner. The above-described RF coil 45 is configured as a coil having transmission and reception functions; however, an RF coil for transmission and an RF coil for reception may be provided separately.

The transmission circuitry 23 transmits to the subject P via the RF coil 45, the high frequency magnetic field to excite the target atomic nucleus, such as a proton, that is present inside the subject P.

The reception circuitry 25 receives the MR signal generated from the excited target atomic nucleus via the RF coil 45. The reception circuitry 25 performs signal processing on the received MR signal to generate a digital MR signal. The digital MR signal is supplied to the processing circuitry 33 in a wired or wireless manner.

The bed 13 is installed adjacent to the gantry 11. The bed 13 includes a top plate 131 and a base 133. The subject P is placed on the top plate 131. The base 133 supports the top plate 131 slidably along each of the X-axis, the Y-axis, and the Z-axis. A bed driving device 135 is housed in the base 133. The bed driving device 135 receives control from the imaging control circuitry 31 and moves the top plate 131. Any motor such as a servomotor and a stepping motor may be used as the bed driving device 135.

The imaging control circuitry 31 controls the gradient magnetic field power supply 21, the transmission circuitry 23, and the reception circuitry 25 in accordance with an imaging protocol output from the processing circuitry 33, and images the subject P. The imaging protocol has different pulse sequences in accordance with the type of examination. The imaging protocol defines the magnitude of a current to be supplied from the gradient magnetic field power supply 21 to the gradient coil 43, the timing at which the current is to be supplied from the gradient magnetic field power supply 21 to the gradient coil 43, the magnitude of an RF pulse to be supplied from the transmission circuitry 23 to the RF coil 45, the timing at which the RP pulse is to be supplied from the transmission circuitry 23 to the RF coil 45, and the timing at which an MR signal is to be received by the reception circuitry 25, etc.

The processing circuitry 33 includes a processor and various types of memories as hardware resources. The processing circuitry 33 includes various types of processing functions such as a system control function 331, a reconstruction function 333, and an image processing function 335. The various types of processing functions such as the system control function 331, the reconstruction function 333, and the image processing function 335 are stored in the storage apparatus 37 in the form of a program that is executable by a computer. The processing circuitry 33 is a processor that realizes a function that corresponds to each program by reading a program that corresponds to each of these functions from the storage apparatus 37 and executing it. In other words, the processing circuitry 33 that has read each program would have each of the functions shown in the processing circuitry 33 of FIG. 2.

In FIG. 2, it is explained that each of the functions is realized by single processing circuitry 33; however, the functions may be realized by configuring the processing circuitry 33 by a combination of a plurality of independent processors, and executing the program by each of the processors. In other words, each of the above-described functions may be configured as a program, and, in some cases, single processing circuitry may execute each program, or a specific function may be implemented in exclusive, independent program-execution circuitry. Each of the system control function 331, the reconstruction function 333, and the image processing function 335 included in the processing circuitry 33 is an example of a system control unit, a reconstruction unit, and an image processing unit.

The term "processor" used in the above explanation indicates circuitry of, for example, a Central Processing Unit (CPU), a Graphics Processing Unit (GPU), an Application Specific Integrated Circuit (ASIC), or a Programmable Logic Device (for example, a Simple Programmable Logic Device (SPLD), a Complex Programmable Logic Device (CPLD), and a Field Programmable Gate Array (FPGA)).

The processor realizes its function by reading and executing a program stored in the storage apparatus 37. Instead of storing the program on the storage apparatus 37, the program may be directly integrated into the circuitry of the processor. In this case, the processor realizes the function by reading and executing the program integrated into the circuit. Similarly, the transmission circuitry 23, the reception circuitry 25, and the imaging control circuitry 31, etc. are also configured by electronic circuitry, such as the above processor.

The processing circuitry 33 integrally controls the MRI apparatus 10 by the system control function 331. Specifically, the processing circuitry 33 reads a system control program stored in the storage apparatus 37, develops it on the memory, and controls each circuitry of the MRI apparatus 10 in accordance with the developed system control program. For example, by the system control function 331, the processing circuitry 33 reads an imaging protocol from the storage apparatus 37 based on conditions for imaging that are input by an operator through interface 36. The processing circuitry 33 outputs the imaging protocol to the imaging control circuitry 31 to control imaging for the subject P.

By the reconstruction function 333, the processing circuitry 33 arranges MR data along a readout direction in a k-space in accordance with a gradient strength of a readout gradient magnetic field. The processing circuitry 33 reconstructs an MR image by performing a Fourier transform on the MR data arranged in the k-space. The processing circuitry 33 outputs the MR image to the display 35 and the storage apparatus 37.

The processing circuitry 33 performs various kinds of image processing on the MR image by the image processing function 335. The processing circuitry 33 outputs the MR image on which the image processing is performed to the display 35 and the storage apparatus 37.

The display 35 displays various types of information. For example, the display 35 displays the reconstructed MR image or the MR image on which the image processing is performed. In addition, the display 35 may display the image projected by the projector 100.

The interface 36 includes circuitry for receiving various instructions and information inputs from an operator. The circuitry in the interface 36 is circuitry regarding a pointing device, such as a mouse, or an input device, such as a keyboard. The circuitry in the interface 36 is not limited to one provided with physical operating parts such as a mouse and a keyboard. Examples of circuitry in the interface 36 include, for example, processing circuitry of an electrical signal that receives the electrical signal corresponding to an input operation from an external input device, provided separately from the MRI apparatus 10, and outputs the received electrical signal to various circuits. The interface 36 may also include circuitry that performs data communication with an external device such as the projector control apparatus 200, the projector 100, and the PACS server via a wired cable, in a wireless manner, or a network, etc.

The storage apparatus 37 stores the MR data that is arranged in the k-space and MR image data, etc. The storage apparatus 37 stores imaging conditions, etc. including various imaging protocols, and a plurality of imaging parameters that define the imaging protocols. The storage apparatus 37 stores programs corresponding to each function executed by the processing circuitry 33. The storage apparatus 37 is, for example, a Random Access Memory (RAM), a semiconductor memory element such as a flash memory, a hard disk drive, a solid state drive, or an optical disk. The storage apparatus 37 may also be a driving device, etc. that reads and writes various information to and from portable storage media, such as a CD-ROM drive, a DVD drive, or a flash memory.

Figure 5:
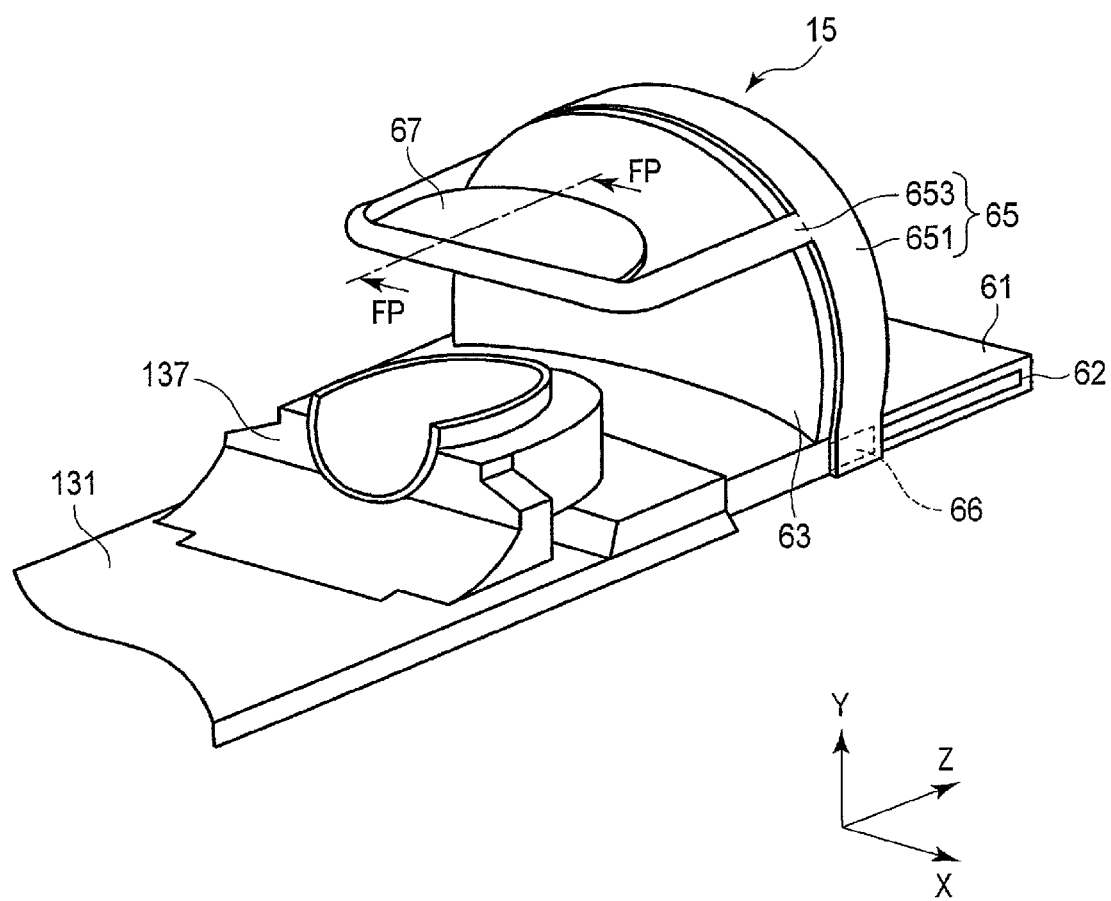
FIG. 5 is a perspective view of the movable screen apparatus and a top plate that are adjacent to each other according to the present embodiment.

In the following, a structure of the movable screen apparatus 15 in the present embodiment will be explained with reference to FIGS. 3 to 5. FIG. 3 is a perspective view of the movable screen apparatus 15 according to the present embodiment. FIG. 4 is a side view of the movable screen apparatus 15. FIG. 5 is a perspective view of the movable screen apparatus 15 and the top plate 131 that are adjacent to each other. As shown in FIG. 3 to FIG. 5, in the case where a screen 63 and a reflector 67 are adopted inside the bore 53 of the MRI apparatus 10, the top plate 131 is fixed via a movable body 61. Preferably, the reflector 67 is arranged directly above a head position on the top plate 131. The reflector 67 may also be mounted on a head coil apparatus.

As shown in FIG. 3 to FIG. 5, the movable screen apparatus 15 includes the movable body 61, the screen 63, the frame 65, and the reflector 67. The movable body 61 supports the screen 63 and the frame 65. The movable body 61 is a structure (carriage) that is movable along a rail (not illustrated) provided in parallel with a central axis Z on an inner wall 57 of the gantry housing 51. The carriage 61 moves through the bore 53. The rail and the movable body 61 are formed by a non-magnetic material that does not affect the magnetic field. On a lower part of the movable body 61 is provided a wheel (not illustrated) that rolls on the rail to enhance traveling performance on the rail. Incidentally, as long as the movable body 61 can travel along the rail, the wheel does not necessarily have to be provided, and a surface in contact with the rail should be formed by a material having a low friction coefficient. Furthermore, instead of the rail and the wheel, a guide such as a linear motion bearing may be provided. As shown in FIG. 5, the movable body 61 and the top plate 131 may be adjacent. Here, together with the top plate 131, the movable body 61 would be movable inside the bore along the central axis Z of the bore 53. A lower coil 137 of the head coil apparatus is attached to the movable body 61 side of the top plate. The lower coil 137 has a curved shape capable of covering an occipital part of the subject P without interrupting the field-of-view of the subject P placed on the back on the top plate 131.

As shown in FIGS. 3 to 5, the screen 63 is provided on the movable body 61. An image from the projector 100 is projected on the screen 63 from the opposite side of the side at which the top plate 131 is inserted into the bore 53. The image is projected on the screen 63 by a projector 100 from a rear. The rear is opposite to a side of which a top plate 131 is inserted into the bore 53. The screen 63 is provided on the carriage 61. In other words, the projector 100 is arranged on the opposite side of the bed 13 with the screen 63 interposed therebetween. At least the upper half of the screen 63 has a shape similar to a cross-sectional shape that is perpendicular to the Z-axis in the bore 53, and is configured in a size that is movable inside the bore. The lower end of the screen 63 has a shape that matches the shape of the movable body 61. Herein, a face of the screen 63 on the projector 100 side is referred to as a front surface, and a face thereof on the bed 13 side is referred to as the rear surface.

The screen 63 is formed by applying on a surface a scattering treatment or a diffusion treatment such as an acrylic, polycarbonate, polyurethane polymer, or olefin polymer transparent base material with non-magnetic properties. Here, a scattering treatment is, for example, surface processing (blast processing), such as a sandblast, or a coating that forms minute concave-convex faces, and a diffusion treatment is, for example, an attachment of various diffusers, such as a micro-prism. Instead of these treatments, white particles may also be dispersed on the transparent base material. The screen 63 is preferably formed using a semi-transparent material in order to allow the image to be projected on the front surface thereof. As such semitransparent material, semitransparent plastic, ground glass, or the like is preferably used.

A projected light emitted from the projector 100 is irradiated on the front surface of the screen 63, and an image corresponding to the projected light is projected on the rear surface. In this manner, the subject P or the like can view the image, which is projected on the screen 63, via the reflector 67. The surface shape of the screen 63 may be a planar shape or a curved shape. In the case where the surface shape of the screen 63 is a curved shape, a convex face thereof is preferred to face the projector 100 side, that is, to be arranged so that the convex face forms the front surface. By facing the convex face to the projector 100 side, it is possible to cover the perimeter of the rear side of the head of the subject P placed on the top plate 131 with the screen 63. In this manner, it is possible to fill the field-of-view of the subject P with the image projected on the screen 63, so that the subject P is immersed in the image.

As shown in FIGS. 3, 4, and 5, the frame 65 is provided on the movable body 61, and supports the reflector 67. Specifically, the frame 65 is provided on the movable body 61 movably along the center axis Z via a connection portion 66 of the frame 65 and the movable body 61. In this manner, the position of the reflector 67 becomes adjustable along the central axis Z. The frame 65 is configured by, for example, a transparent material. This allows the sense of pressure caused by the frame 65 to the subject P to be reduced. The connection portion 66 corresponds to a contact surface between the linear motion bearing and a guide rail 62. The connection portion 66 is provided at a position on the movable body 61 where it would not interrupt the image projected on the screen 63 from the projector 100.

The frame 65 includes a first support portion 651 and a second support portion 653. The lower end of the first support portion 651 is provided on the movable body 61 via an unillustrated linear motion bearing and the guide rail 62. The first support portion 651 is, for example, an arch member that has a curved shape along the inner wall 57 of the bore 53. The shape of the first support portion 651 is not limited to the above-mentioned shape as long as it is a shape that does not interrupt the image projected on the screen 63 from the projector 100. The second support portion 653 is an arm member that extends from the first support portion 651 to the bed 13 side over the screen 63. For example, the second support portion 653 supports the reflector 67 over the screen 63 by being passed through a space between an exterior edge of the screen 63 above a middle point of an upper end and a lower end of the screen 63 and the inner wall 57 of the bore 53.

As shown in FIG. 4, the second support portion 653 supports the reflector 67 in a rotatable manner about a rotary axis RR1 by a rotation mechanism (not illustrated) provided on the second support portion 653. For example, the rotary axis RR1 is provided in parallel with the X-axis so as to be able to adjust a direction of the reflector 67 with respect to the screen 63. The structure of the second support portion 653 is not limited to that described in FIGS. 3 to FIG. 5. For example, the second support portion 653 may be an arm member that extends from an upper end of the first support portion 651, beyond the screen 63 along the central axis Z of the bore 53, to a position immediately above the lower coil 137.

The reflector 67 reflects an image displayed at the rear. The reflector 67 reflects the image projected on the screen 63. The reflected image is seen from the subject P facing up on the top plate 131. Specifically, the reflector 67 is spaced apart from the surface of the carriage 61 to a degree that would not collide with the head of the subject P placed on the top plate 131, or with the head coil apparatus in a state where the carriage 61 and the top plate 131 are coupled with each other, and is supported by the second support portion 653 of the frame 65. As shown in FIGS. 3 to 5, the reflector 67 is provided at substantially the end of the second support portion 653 on the bed 13 side. The reflector 67 reflects the image projected on the front surface of the screen 63. The reflector 67 is configured by a non-magnetic material. In consideration of, for example, weight reduction and safety, the reflector 67 is preferably configured by a plastic mirror. The plastic mirror is made by forming a mirror thin film (reflection film) having reflective characteristics onto a transparent plastic. The mirror thin film is preferably a dielectric multilayer film of a non-magnetic material rather than a metal thin film. The subject P whose head is placed on the lower coil 137 can view the image projected on the screen 63 via the reflector 67. At this time, the reflector 67 is arranged tilted against a horizontal direction in order to reflect the image projected on the screen 63 along the line of sight of the subject P. The reflector 67 may also provide an image to the subject P placed on the top plate 131 by reflecting the image displayed on an opposite side of a side at which the top plate 131 is inserted into the bore 53.

In the case where, for example, the bore 53 formed in the gantry housing 51 is configured by a narrow bore, such as a bore diameter of approximately 60 cm, a distance between a position of an eye of the subject P placed on the top plate 131 and the inner wall 57 of the bore 53 would be equal to or less than 20 cm. Furthermore, in the case where the head coil apparatus is worn on the subject P, a distance from the uppermost position of the head coil apparatus to the inner wall 57 of the bore 53 would, for example, be less than 10 cm. Therefore, when using the narrow bore or the head coil apparatus, it would be difficult to tilt the reflector 67 against the horizontal direction in order to provide the image projected on the screen 63 via a regular reflection at the reflector 67 to the subject P. In the following, a structure of the reflector 67 that overcomes the above-mentioned difficulty will be explained.

Figure 6:
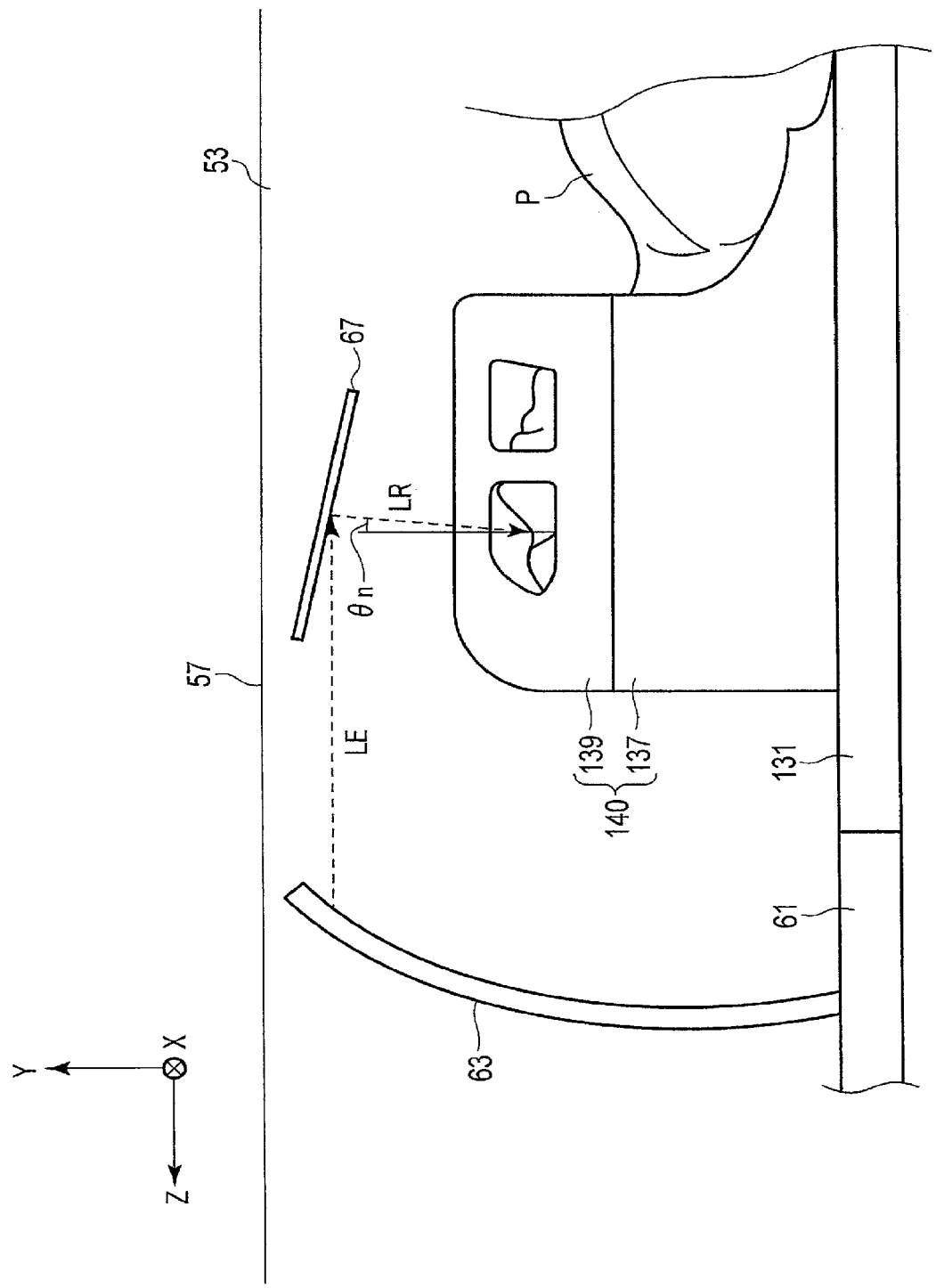
FIG. 6 shows an example of a positional relationship of a screen, a reflector, and a subject wearing a head coil apparatus according to the present embodiment.
Figure 7:
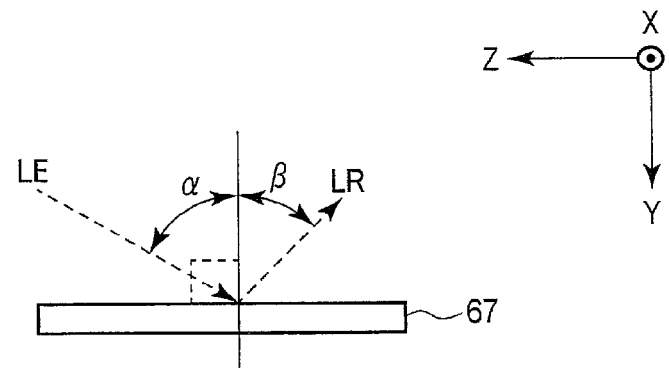
FIG. 7 shows an example of a reflection characteristic at the reflector according to the present embodiment.

The reflector 67 has a structure that performs reflection in a direction different from a regular reflection direction with respect to an incident direction of a light. This reflector 67 allows the image projected on the screen 63 to be provided to the subject P even when using the narrow bore or the head coil apparatus. FIG. 6 shows an example of a positional relationship of the screen 63, the reflector 67, and the subject P wearing the head coil apparatus 140. FIG. 7 shows an example of a reflection characteristic at the reflector 67. As shown in FIG. 6, the reflector 67 is tilted in a tilted angle that avoids contact with the subject P and an upper coil 139 of the head coil apparatus 140. The dotted lines in FIG. 6 and FIG. 7 show an example of a light LE incident on the reflector 67 in a horizontal direction being reflected at the reflector 67, and a reflected light LR along an angle θn against a vertical direction Y reaching the eye of the subject P. Here, the reflected light LR along the angle θn is an example of a center line of the field-of-view of the subject P.

The reflector 67 is tilted so that the end (hereinafter referred to as an upper end) of the reflector 67 that is closer to the screen 63 than the end (hereinafter referred to as a lower end) of the reflector 67 spaced apart from the screen 63 becomes closer to the inner wall 57 of the bore 53. Furthermore, the reflector 67 is tilted so that the lower end of the reflector 67 becomes closer to the subject P than the upper end of the reflector 67. The angle of the reflector 67 for providing the image projected on the screen 63 to the subject P may be horizontal as well. As shown in FIG. 7, the reflector 67 in the present embodiment performs reflection in a direction LR that is different from a regular reflection direction with respect to the incident direction LE of the light. In other words, a reflection angle is set so that a reflection angle β is smaller than a light incident angle a at the reflector 67 ($\alpha > \beta$). Specifically, the reflection angle is set to an angle at which an image light emitted from the screen 63 is reflected by the reflector 67 and is reflected in the direction of the eye of the subject P.

Required conditions for the reflection angle are for the subject P placed on the top plate 131 to be able to observe the image projected on the screen 63. Hereinafter, the required conditions will be explained. The size of the reflector 67 is preferably a size that includes a range of the field-of-view of the subject P. Here, since the inner wall 57 of the bore 53 does not come into the range of the field-of-view of the subject P placed on the top plate 131, the sense of immersion of the subject P into the image projected on the screen 63 is enhanced. In order to make the subject P placed on the top plate 131 unaware of the inner wall 57 of the bore 53, for example, the length of the reflector 67 along the X-axis direction is preferred to be a length that is included in a range of at least 60 degrees each to the left and to the right from a central line of the field-of-view of the subject P. The length along the X-axis direction at the reflector 67 is set based on, for example, a distance from the top plate 131 to the inner wall 57 of the bore 53. In the case where the screen 63 is a plane screen, the reflector 67 may be curved with a convex part facing the top plate 131 side.

In the following, a maximum limit condition for allowing a part of the image projected on the screen 63 via the reflector 67 to be visually recognized by the subject P placed on the top plate 131 will be explained. Here, two maximum limit conditions exist. The first maximum limit condition is a condition for the subject P to visually recognize an upper end of the screen 63 via a lower end of the reflector 67, which is a condition of a lower field-of-view side of the subject P (hereinafter referred to as a lower field-of-view maximum limit condition). The second maximum limit condition is a condition for the subject P to visually recognize a lower end of the screen 63 via an upper end of the reflector 67, which is a condition of an upper field-of-view side of the subject P (hereinafter referred to as an upper field-of-view maximum limit condition).

First, the lower field-of-view maximum limit condition in which the upper end of the screen 63 is visually recognized will be explained. To provide a specific explanation, the size of the reflector 67 is assumed to be a narrowly defined field-of-view range. The narrowly defined field-of-view range corresponds to, for example, a range from 60 degrees to 130 degrees on the basis of a horizontal surface for the subject P placed on the top plate 131. Here, the lower field-of-view maximum limit condition for reflecting the upper end of the screen 63 in the lower end of the reflector 67 is satisfied when a straight line joining the upper end of the screen 63 and the lower end of the reflector 67 becomes horizontal. In this lower field-of-view maximum limit condition, when the image projected on the screen 63 is reflected by the reflector 67 and reaches the eye of the subject P, an arrangement angle of a virtual mirror surface, that is, the tilted angle of the mirror to perform regular reflection, becomes, for example, 65 degrees from the horizontal surface. Here, an angle of a normal line azimuth of the virtual mirror surface becomes -25 degrees. The arrangement angle of the reflector 67 is set in a range that avoids contact with the inner wall 57 of the bore 53 and the subject P. Here, when the arrangement angle of the reflector 67 with respect to the horizontal surface is $\alpha 1$, and the reflection angle at the reflector 67 is $\alpha 2$, the arrangement angle of the virtual mirror surface corresponds to a sum of the arrangement angle al of the reflector 67 and the reflection angle $\alpha 2$ at the reflector 67 ($\alpha 1 + \alpha 2$: hereinafter referred to as a setting angle).

Next, the upper field-of-view maximum limit condition will be explained. The upper field-of-view maximum limit condition for reflecting the lower end of the screen 63 in the upper end of the reflector 67 is satisfied when a normal line of the virtual mirror surface becomes perpendicular, that is, the arrangement angle of the virtual mirror surface becomes 0 degree. In this upper field-of-view maximum limit condition, the lower end of the screen 63 is reflected in the upper end of the reflector 67. In the upper field-of-view maximum limit condition, in order to tilt the normal line of the virtual mirror surface to the screen 63 side, it is necessary to move the reflector 67 in the horizontal direction. Actually, the arrangement angle of the reflector 67 is set in a range that avoids contact with the inner wall 57 of the bore 53 and the subject P. According to the lower field-of-view maximum limit condition and the upper field-of-view maximum limit condition mentioned above, the image projected on the screen 63 becomes upside down by the reflector 67, that is, becomes reversed with respect to the Y-axis direction. Therefore, the image projected on the screen 63 from the projector 100 is reversed upside down in advance in order to have the image visually recognized in an upright state by the subject P.

In fact, depending on the arrangement angle of the reflector 67, a face of the subject P may sometimes be reflected on the reflector 67. Therefore, a condition for preventing the face of the subject P from being reflected on the reflector 67 will be explained. In order to satisfy this condition, the arrangement angle of the reflector 67 and the reflection angle of the reflector 67 are set in the following manner. First of all, an angle between a tangent that passes through the lower end of the reflector 67 and comes in contact with the head of the subject P, and a straight line that joins the lower end of the reflector 67 and the position of the eye of the subject P, is obtained. The arrangement angle al of the reflector 67 and the reflection angle α2 at the reflector 67 are set so that a bisector of the obtained angle becomes a setting angle (α1+α2) of the reflector 67. In the upper field-of-view of the subject P, in order for the subject P to visually recognize the upper end of the screen 63 as much as possible, it is necessary to set the reflector 67 as horizontal as possible. Therefore, the upper end of the reflector 67 is preferably arranged on a line extending in a horizontal direction of the upper end position of the screen 63 in the manner shown in FIG. 6.

Figure 8:
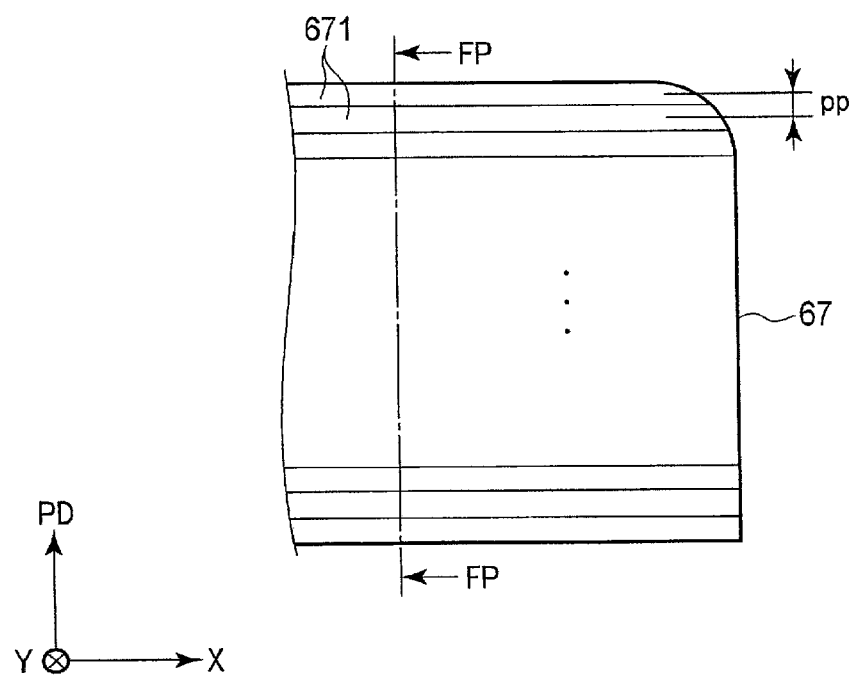
FIG. 8 is a view of viewing the reflector from a placement surface side of the top plate according to the present embodiment.

Hereinafter, a further detailed structure of the reflector 67 will be explained. FIG. 8 is a view of viewing the reflector 67 from a placement surface side of the top plate 131. As shown in FIG. 8, a plurality of prisms (multi-prisms) 671 are formed on the top plate 131 side (hereinafter referred to as a front surface) of the reflector 67. The reflector 67 includes a plurality of prisms 671 arranged in a same line. The line is parallel to a moving direction of the top plate 131 when viewed from a direction along the moving direction. In other words, the plurality of prisms 671 are provided on an incident surface side of the reflector 67 upon which light regarding the image projected on the screen 63 is incident. The incident surface receives a light related to the image. The plurality of prisms 671 may also be provided on the inner wall 57 side of the bore 53 (hereinafter referred to as a rear surface) on the reflector 67. The plurality of prisms 671 are arranged perpendicular to the incident direction of an image, along a singular dimensional direction, and not in an orbicular zone. In this manner, the subject P is able to observe the image projected on the screen 63 via the plurality of prisms 671 on the reflector 67.

As shown in FIG. 8, a one-dimensional direction is a direction PD in which the moving direction (Z-axis direction) of the top plate 131 in the bore 53 is projected on the reflector 67. Each of the prisms is extended in a direction different from the one-dimensional direction. The different direction is, for example, a short axis direction (X-axis direction) of the top plate 131. Each of the prisms may be extended curving in the one-dimensional direction PD in the manner shown in FIG. 9. The each of the prisms extends along a direction that is different from the line, and curves in the line of the reflector 67. FIG. 9 is a view of viewing the reflector 67 including a plurality of prisms curved in a one-dimensional direction PD from the placement surface side of the top plate 131. The extent of curvature in the one-dimensional direction PD at each of the prisms may be different from each other. The extent of curvature to the line differs between each of the prisms. The extent of curvature at each of the prisms is set to secure redundancy regarding resolution of a reflected image of an image projected on the screen 63, and resolution and a range of the field-of-view that tolerates individual differences in the position of the eye of the subject P on the top plate 131. The extent of curvature at each of the prisms may also be set in accordance with the extent of curvature of the shape of the reflector 67. Furthermore, instead of the prism, a holographic sheet may be used.

At the plurality of prisms 671, an interval (hereinafter referred to as prism pitch) pp of two prisms adjacent to each other is set in accordance with the resolution of a reflected image of the image projected on the screen 63. The prism pitch pp is preferred to be equal to or less than 0.5 mm, which is less affected by a deterioration of resolution caused by reflection of an image by the prism. Each of the prism pitches pp may also be different in order to maintain a desired resolution of the image visually recognized by the subject P via the reflector 67, and to secure the above-mentioned redundancy.

The base material of the reflector 67 may be either glass or plastic; however, in consideration of its lightweight properties and workability, plastic is preferable. For example, as a base material of the reflector 67, acryl, polycarbonate, polyurethane plastic, polyolefin plastic, and epoxy resin, etc. are used. On these base materials minute micro-prisms are formed. As a method of forming micro-prisms, a general plastic forming technique using a mold that transfers a prism shape is used to transfer the prism shape by a hot press, injection molding or polymerization molding, etc. By coating a reflection film (mirror coating) on the surface of each of the prisms, a mirror effect is produced for each of the prisms. Hereinafter, a prism having a mirror effect will be referred to as a prism mirror.

For the mirror coating, other than the metal thin film formed of aluminum or silver, etc., a reflection film using a dielectric multi-layer film can be used. In most cases, the dielectric multi-layer film is formed by an inorganic multi-layer film of such as $SiO_2$, $TiO$, $Al_2O_3$, or $ZrO$. Higher reflectances are preferred. Brightness of the reflected image will be secured if the reflectance is, for example, at least 70%, or, preferably, at least 85%. By the above method, on the base material of the reflector 67, a plurality of prisms 671 are formed as a one-dimensional multi-prism mirror arranged along the first dimensional direction PD.

FIG. 10 is an arrow cross-sectional view taken along line FP-FP in FIG. 5 and FIG. 8. As shown in FIG. 10, on the front surface facing the top plate 131 on a base material 673 of the reflector 67, a plurality of prisms 671 are arranged saw-like along the one-dimensional direction PD. The prism pitch pp in FIG. 10 is equidistant; however, as mentioned above, in order to maintain a desired resolution that is independent of the position of the eye that differs for each subject, each of the prism pitches pp may be different. For each of the prisms 671, the reflection film 675 is provided on the front surface (hereinafter referred to as a prism surface) facing the top plate 131. For the plurality of prisms shown in FIG. 10, an angle (hereinafter referred to as a prism angle) θf between the base substrate 673 and the prism surface, that is, a tilted angle of the prism surface with respect to a horizontal surface in a state where the reflector 67 is arranged horizontally, is constant across the plurality of prisms 671. The prism angle θf in each of the prisms 671 is set larger than the tilted angle of the reflector 67 with respect to the horizontal surface shown in FIG. 6.

In order to maintain a desired resolution that is independent of the position of the eye that is different for each subject, at least one of the prism angle θf and the prism pitch pp may be set differently for each of the plurality of prisms 671 in accordance with the position of each of the prisms 671 on the reflector 67; for example, a distance from a center position of the reflector 67, the shape of the screen 63, the inner diameter of the bore 53, and a relative position of the reflector 67 with respect to the screen 63. An example in which each of the prisms 671 has a structure extending in the X-axis direction, and is arranged on the base material along the one-dimensional direction PD has been explained; however, the prism 671 is not limited thereto. For example, the shape of the contact surface between the plurality of prisms 671 and the base material 673 may be rectangular. In this case, each of the prisms is arranged two-dimensionally on the base material 673. For example, in order to maintain a desired resolution that is independent of the position of the eye that is different for each subject, the plurality of prisms with rectangular contact surfaces are arranged two-dimensionally on the base material 673 in accordance with a distance from a center position of the reflector 67, the shape of the screen 63, the inner diameter of the bore 53, and a relative position of the reflector 67 with respect to the screen 63.

According to the configurations mentioned above, the following effects may be obtained.

The medical imaging apparatus 10 according to the present embodiment comprises a screen 63 that is provided on a movable body 61 that is movable inside a bore 53 formed in a gantry 11 that comprises a medical imaging mechanism, and on which an image from a projector 100 is projected from an opposite side of a side of which a top plate 131 is inserted into the bore 53, and a frame 65 that is provided on the movable body 61, and supports a reflector 67 that reflects the image projected on the screen 63. The reflector 67 has a structure (a one-dimensional multi-prism structure) in which a plurality of prisms 671 are arranged along a one-dimensional direction PD that projects a movable direction of the top plate 131 inside the bore 53 on the reflector 67.

According to the present embodiment, each of the prisms 671 can be extended along a direction that is different from the one-dimensional direction PD, and curved in the one-dimensional direction PD. Here, the extent of curvature in the one-dimensional direction PD can be changed for each of the prisms 671. According to the present embodiment, for each of the prisms 671, the tilted angle of the prism surface with respect to the horizontal surface can be made larger than the tilted angle of the reflector 67 with respect to the horizontal surface. According to the present embodiment, at least one of the tilted angle θf and the prism pitch pp of the prism surface can be changed for each of the prisms 671, and the prism pitch can be made equal to or less than 0.5 mm. According to the present embodiment, on the reflector 67, the plurality of prisms 671 can be provided on an incident surface side of which light regarding the image is incident upon the reflector 67.

Therefore, according to the medical imaging apparatus 10 of the present embodiment, by providing a structure (prism mirror) that performs reflection in a direction different from a regular reflection direction against an incident direction of a light on the reflector 67, an image projected on the screen 63 can be provided to the subject P even when using a narrow bore or a head coil apparatus 140. In addition, according to the present embodiment, by providing the one-dimensional multi-prism structure on the front surface of the reflector 67, individual differences of the position of the eye of the subject P on the top plate 131 can be accommodated. Therefore, according to the present embodiment, the subject P's sense of being blocked inside the bore 53 of the gantry 11 can be reduced.

Applied Examples

The difference from the present embodiment is that an enlargement function that enlarges an image reflected on a reflector 67 is added to the reflector 67. A plurality of prisms 671 in the present applied example are provided on a rear surface of the reflector 67 on a base material 673 thereof. The enlargement function is realized by providing an optical power or a Fresnel lens on a front surface side of the reflector 67 on the base material thereof. Here, the optical power corresponds to an inverse number of a focal distance of the lens, which, in the present applied example, corresponds to a "diopter" in a lens where a top plate 131 side is convex. Hereinafter, a structure regarding the enlargement function of the reflector 67 will be explained.

FIG. 11 is an arrow cross-sectional view taken along line FP-FP of FIG. 5 and FIG. 8 in the present applied example. As shown in FIG. 11, at the reflector 67, a convex transparent lens (hereinafter referred to as a convex lens) that has a convex portion on the top plate 131 side, is formed on an incident surface of which a light regarding an image projected on a screen 63 is incident upon the reflector 67. In addition, at the reflector 67 shown in FIG. 11, a plurality of prisms 671 are formed on a facing surface that faces this incident surface. In other words, on the top plate 131 side of the plurality of prisms 671 having a reflection film 675 that reflects an image, a base material 673 of the reflector 67 becomes the convex lens. The image projected on the screen 63 is enlarged by the convex lens. Therefore, a subject P placed on the top plate 131 is able to visually recognize the enlarged image. The surface shape of the convex lens may be either spherical or aspherical. As shown in FIG. 11, a reflection film 675 that reflects a light that reflects the image is arranged on the opposite side of the screen 63 with respect to the base material 673. A convex lens power surface 677 that enlarges the image reflected by the reflection film 675 is arranged on the screen 63 side with respect to the base material 673. An anti-reflective (AR) coating for preventing reflection is preferred to be applied on the surface of the lens power surface 677.

Since the convex lens having an optical power causes the thickness of the reflector 67 to increase, the reflector 67's own weight increases. Therefore, degradation in the operability of the reflector 67, and an increase in the cost for enhancing rigidity of the frame 65 are matters of concern. In order to solve these concerns, it is effective to use a Fresnel structure that reduces weight and thickness as the base material 673 having the enlargement function, that is, the lens portion. By using acryl or polycarbonate, or a transparent optical plastic such as a polyolefin transparent plastic material or a polyurethane transparent plastic material, the reflector 67 can be made lighter. The pitch of the groove of the lens in the Fresnel structure is preferably equal to or less than 0.5 mm, and is more preferably equal to or less than 0.3 mm.

FIG. 12 is an arrow cross-sectional view taken along line FP-FP of FIG. 5 and FIG. 8 in the present applied example. As shown in FIG. 12, at the reflector 67, a Fresnel lens 679 is formed on an incident surface of which a light related to an image projected on the screen 63 is incident upon the reflector 67. In addition, at the reflector 67 shown in FIG. 12, a plurality of prisms 671 are formed on a facing surface that faces this incident surface. The image projected on the screen 63 is enlarged by the Fresnel lens 679. Therefore, a subject P placed on the top plate 131 is able to visually recognize the enlarged image. As shown in FIG. 12, a reflection film 675 that reflects a light reflecting the image is arranged on the opposite side of the screen 63 with respect to the base material 673. An anti-reflective (AR) coating for preventing reflection is preferred to be applied on the surface of the Fresnel lens 679.

According to the configuration mentioned above, in addition to the effects of the present embodiment, the following effects may be obtained.

According to the medical imaging apparatus 10 of the applied example of the present embodiment, at the reflector 67, a convex lens can be formed on an incident surface of which a light related to an image projected on the screen 63 is incident upon the reflector 67, and a plurality of prisms 671 can be formed on a facing surface that faces this incident surface. Furthermore, according to the present applied example, at the reflector 67, a Fresnel lens can be formed on an incident surface of which a light regarding an image projected on the screen 63 is incident upon the reflector 67, and a plurality of prisms 671 can be formed on a facing surface that faces this incident surface.

In this manner, according to the present applied example, the image projected on the screen 63 can be enlarged, and a subject P placed on the top plate 131 can visually recognize the enlarged image. Furthermore, according to the present applied example, even if the screen 63 is a plane screen, an image with a sense of openness can be provided to the subject P, which allows to further reduce a sense of blockage for the subject P inside the bore 53 of the gantry 11.

According to the medical imaging apparatus of the above-mentioned embodiment and applied example, etc., it is possible to attempt to reduce the subject P's sense of being blocked inside the bore 53 of the gantry 11.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical imaging apparatus comprising:
a gantry in which a bore is formed, the bore being formed to accept a patient to be imaged by the medical imaging apparatus;
a carriage configured to move through the bore;
a screen on which an image is projected from a rear, the rear being opposite to a side of which a top plate is inserted into the bore, the screen being provided on the carriage;
a reflector configured to reflect the image projected on the screen, the reflector including a base having a surface, and a plurality of projecting prisms arranged on the surface of the base, perpendicular to an incident direction of the image, and adjacent to one another along a singular dimensional direction,
wherein each of the prisms extends in a direction parallel to a plane of the surface of the base and curves within the plane of the surface of the base, and wherein each of the prisms has a different extent of curvature within the plane of the surface of the base; and
a frame configured to support the reflector, the frame being provided on the carriage,
wherein the reflector receives a light related to the image directly from the screen, and the plurality of prisms reflect the light to the patient.

2. The medical imaging apparatus according to claim 1, wherein in each of the prisms, a tilted angle of a prism surface with respect to a horizontal surface is larger than a tilted angle of the reflector with respect to the horizontal surface.

3. The medical imaging apparatus according to claim 2, wherein the tilted angle of the prism surface differs between each of the prisms.

4. The medical imaging apparatus according to claim 1, wherein a convex lens is formed on an incident surface of the reflector, the incident surface receiving a light related to the image, and the plurality of prisms are formed on opposite side of the incident surface.

5. The medical imaging apparatus according to claim 1, wherein the plurality of prisms are of a prism mirror.

6. A medical imaging apparatus, comprising:
a gantry in which a bore is formed, the bore being formed to accept a patient to be imaged by the medical imaging apparatus; and
a reflector configured to reflect an image displayed at a rear, the rear being opposite to a side of which a top plate is inserted into the bore, the reflected image being seen from a patient facing up on the top plate, the reflector including a base having a surface, and a plurality of projecting prisms arranged on the surface of the base, perpendicular to an incident direction of the image, and adjacent to one another along a singular dimensional direction,
wherein each of the prisms extends in a direction parallel to a plane of the surface of the base and curves within the plane of the surface of the base, and wherein each of the prisms has a different extent of curvature within the plane of the surface of the base; and
wherein the reflector receives a light related to the image directly from the rear, and the plurality of prisms reflect the light to the patient.

7. A medical imaging apparatus comprising:
a gantry in which a bore is formed, the bore being formed to accept a patient to be imaged by the medical imaging apparatus;
a carriage configured to move through the bore;
a projector;
a screen on which an image is projected by the projector from a rear, the rear being opposite to a side of which a top plate is inserted into the bore, the screen being provided on the carriage;
a reflector configured to reflect the image projected on the screen, the reflector including a base having a surface, and a plurality of projecting prisms arranged on the surface of the base, perpendicular to an incident direction of the image, and adjacent to one another along a singular dimensional direction,
wherein each of the prisms extends in a direction parallel to a plane of the surface of the base and curves within the plane of the surface of the base, and wherein each of the prisms has a different extent of curvature within the plane of the surface of the base; and a frame configured to support the reflector, the frame being provided on the carriage, wherein the reflector receives a light related to the image directly from the screen, and the plurality of prisms reflect the light to the patient.

8. The medical imaging apparatus according to claim 7, wherein in each of the prisms, a tilted angle of a prism surface with respect to a horizontal surface is larger than a tilted angle of the reflector with respect to the horizontal surface.

9. The medical imaging apparatus according to claim 8, wherein the tilted angle of the prism surface differs between each of the prisms.

* * * * *